United States Patent
Bieniosek et al.

(10) Patent No.: US 8,902,097 B2
(45) Date of Patent: Dec. 2, 2014

(54) NON-LINEAR DATA ACQUISITION (75) Inventors: Matthew Bieniosek, Stanford, CA (US); Hans Weedon, Salem, MA (US); Enrico Dolazza, Boston, MA (US); Martin Choquette, Exeter, NH (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 13/876,156

(22) PCT Filed: Sep. 30, 2010

(86) PCT No.: PCT/US2010/050957
§ 371 (c)(1),
(2), (4) Date: Mar. 26, 2013

(87) PCT Pub. No.: WO2012/044311
PCT Pub. Date: Apr. 5, 2012

(65) Prior Publication Data
US 2013/0188777 A1    Jul. 25, 2013

(51) Int. Cl.
*H03M 1/58* (2006.01)
*H05G 1/08* (2006.01)
*H03M 1/12* (2006.01)

(52) U.S. Cl.
CPC . *H05G 1/08* (2013.01); *H03M 1/58* (2013.01); *H03M 1/123* (2013.01)
USPC ........... 341/170; 341/155; 341/165; 341/167; 378/91; 378/207

(58) Field of Classification Search
CPC ........ H05G 1/08; H03M 1/123; H03M 1/502; H03M 1/1235; H03M 1/58; G09G 1/04; H03L 1/023
USPC .............................. 341/144–170; 378/91, 207
See application file for complete search history.

(56) References Cited

U.S. PATENT DOCUMENTS

| 4,569,028 A | 2/1986 | Dolazza et al. |
| 5,138,552 A | 8/1992 | Weedon et al. |

(Continued)

FOREIGN PATENT DOCUMENTS

| JP | 1986-253934 | 11/1986 |
| JP | 2001-145626 | 5/2001 |

(Continued)

OTHER PUBLICATIONS

International Search Report cited in related application No. PCT/US2010/050957 dated Aug. 11, 2011.
Snoeij, et al., "Multiple-Ramp Column-Parallel ADC Architectures for CMOS Image Sensors" shows a method of using multiple linear slopes to make a piecewise approximation of a parabolic ramp, IEEE Journal of Solid State Circuits, IEEE Journal of Solid-State Circuits, vol. 42, No. 12, Dec. 2007, pp. 2968-2977.

(Continued)

*Primary Examiner* — Lam T Mai
(74) *Attorney, Agent, or Firm* — Cooper Legal Group LLC (57) ABSTRACT

One or more techniques and/or systems described herein implement, among other things, a parabolic curve for a ramp signal in a data acquisition component, where the curve can be effectively calibrated and used to provide a settling period to mitigate noise. That is, a ramp generator can generate a ramp signal that has a parabolic voltage curve with two substantially mirroring halves. A comparator can compare a first portion of the parabolic voltage curve with a voltage signal indicative of a number of photons detected by a detection array. A second portion of the parabolic voltage curve is used as a temporal delay so that circuitry, such as the ramp generator, can settle.

22 Claims, 7 Drawing Sheets

(56) References Cited

U.S. PATENT DOCUMENTS

| | | | | |
|---|---|---|---|---|
| 6,545,624 | B2* | 4/2003 | Lee et al. | 341/170 |
| 7,541,963 | B2* | 6/2009 | Krymski | 341/170 |
| 7,612,702 | B2* | 11/2009 | Danesh | 341/170 |
| 8,054,209 | B2* | 11/2011 | Krymski | 341/170 |
| 8,237,599 | B2* | 8/2012 | Marrero et al. | 341/170 |

FOREIGN PATENT DOCUMENTS

| | | |
|---|---|---|
| JP | 2009-188815 | 8/2009 |
| JP | 2009-219538 | 10/2009 |
| WO | 2005/011502 A1 | 2/2005 |

OTHER PUBLICATIONS

Bieniosek, Matthew, "A Square Root Analog to Digital Converter to Optimally Convert Photonic Signals for Computed Tomograhy", http://dspace.mit.edu/bitstream/handle/1721.1/62309/710219017. pdf? . . . 1, pp. 1-69, Mar. 31, 2011.

Dolazza, et al., "Optimal Quantization of Noisy Signals", Proc. SPIE 0454, Application of Optical Instrumentation in Medicine XII, 403 (Jun. 15, 1984); doi:10.1117/12.939361, http://proceedings. spiedigitallibrary.org/proceeding.aspx?articleid=1236976. pp. 1-16.

Japanese Office Action cited in Japanese Application No. 2013-531550 dated Jun. 2, 2014, 8 pgs.

* cited by examiner

NON-LINEAR DATA ACQUISITION

BACKGROUND

The present application relates to the field of imaging, such as particle detection, radiographic imaging, photography, etc. It finds particular application with medical, security, and/or other applications where measuring discrete events to obtain an image of an object may be useful, but it is not intended to be limited to merely the same.

Imaging systems, such as computed tomography (CT) systems, line scanners, etc., provide information, or images, of an object under examination (e.g., interior aspects an object under examination). For example, in radiographic imaging systems, the object is exposed to radiation, and one or more images are formed based upon the radiation absorbed by the object, or rather an amount of radiation that is able to pass through the object. Typically, highly dense objects absorb (e.g., attenuate) more radiation than less dense objects, and thus an object having a higher density, such as a bone or gun, for example, will be apparent when surrounded by less dense objects, such as fatty tissue or clothing, for example. A detector array, generally positioned opposite a radiation source from which radiation is emitted relative the object under examination, is configured to detect radiation that traverses the object under examination and convert such radiation into signals and/or data that may be processed to produce the image(s). Such an image(s) may be viewed by security personnel to detect threat items (e.g., weapons, etc.) and/or viewed by medical personnel to detect medical conditions (e.g., cancerous tissue), for example.

In some scanners, such as three-dimensional radiographic imaging scanners (e.g., CT scanners), for example, the detector array and radiation source are mounted on opposing sides of a rotating gantry that forms a ring, or toroid, around the object under examination. In such a scanner, the rotating gantry (including the radiation source and/or detector array) is rotated in a circle situated within an x, y plane about a z-axis substantially perpendicular to the x, y plane (e.g., an "isocenter") during an examination. The object is generally supported by a support article (e.g., a bed, conveyor belt, etc.) that runs in the z direction substantially parallel to the mechanical center of rotation (e.g., the isocenter). As the rotating gantry is rotated, radiation is substantially continuously emitted from a focal spot of the radiation source toward the object under examination.

Radiation photons that impinge the detector array can be converted into a current or voltage, and a corresponding analog signal, that is representative of, or directly proportional to, the number of photons detected can be produced. For example, a higher voltage signal may correspond to more detected photons and a lower voltage signal may correspond to fewer detected photons.

Analog to digital converters (A/D) are often used in imaging systems to convert an analog signal, such as a voltage signal proportional to a number of detected photons, to a digital signal, where a digital signal may be more easily used for image reconstruction, for example. One type of ADC is the ramp ADC. An unknown input (e.g., indicative of a number of detected photons) is compared against a known input (e.g., a ramp signal), and a time it takes for the two signals to meet (e.g., have equal voltage levels) can be used as the digital output (e.g., number of timed sampling units). One of the more common types of ramp signals is a linear ramp signal, which is characterized by a voltage that increases at a constant rate. While this type of ramp has proven useful, it has several disadvantages. For example, identifying the voltage of an unknown signal from a linear ramp signal is time consuming because the sampling units (e.g., codes) are evenly distributed even though a non-uniform distribution of fewer units may provide the same or similar accuracy. For example, where a relatively large number of photons are detected (e.g., hundreds of thousands), fewer sampling units are necessary because the effect of missing a few photons (e.g., due to a lack of samplings) may be relatively insignificant given the large noise inherent to the signal and the large number of photons detected (e.g., as indicated by higher voltage signals). On the other hand, where a relatively small number of photons are detected (e.g., less than one hundred), more sampling units are necessary because the effect of missing a few photons (e.g., due to a lack of samplings) may be relatively significant given the relatively small photon noise and the small number of photons detected (e.g., as indicated by lower voltage signals). Thus, because the number of sampling units used for higher voltage signals (e.g., indicative of more photons) is generally the same as the number of sampling units used for lower voltage signals (e.g., indicative of fewer photons), more time is taken than is needed in conventional systems because fewer sampling units are needed for the higher voltage signals. Moreover, because of the high number of sampling units, the amount of data that is produced is large and may need to be compressed before transmission from a rotating gantry portion of a scanner to a stationary portion, for example, requiring additional resources and/or overhead.

More recently, non-linear ramp signals, such as logarithmic or square ramp signals, have been utilized because these ramp signals typically overcome at least some of the disadvantages of linear ramp signals. For example, non-linear ramp signals have been used because such signals generally require fewer sampling units, and thus take less time. Stated differently, at levels indicative of more photons (e.g., higher voltage signals) the number of sampling units used is less than the number of sampling units used at levels indicative of fewer photons (e.g., lower voltage signals), thus reducing overall time. Moreover, because the number of sampling units is fewer, the amount of data generated from a scan is less than the amount of data generated if a linear ramp where used. Thus, little to no data compression may be required to transfer the data from a rotating gantry portion of the scanner to a stationary portion of the scanner, for example.

While non-linear ramp signals overcome many of the disadvantages of linear ramp signals, non-linear ramp signals also have some disadvantages. For example, these ramps require high bandwidth circuits to generate the ramps quickly and accurately. Such circuits are costly to manufacturer and may introduce electronic and/or other types of noise into the system.

SUMMARY

Figure 1:
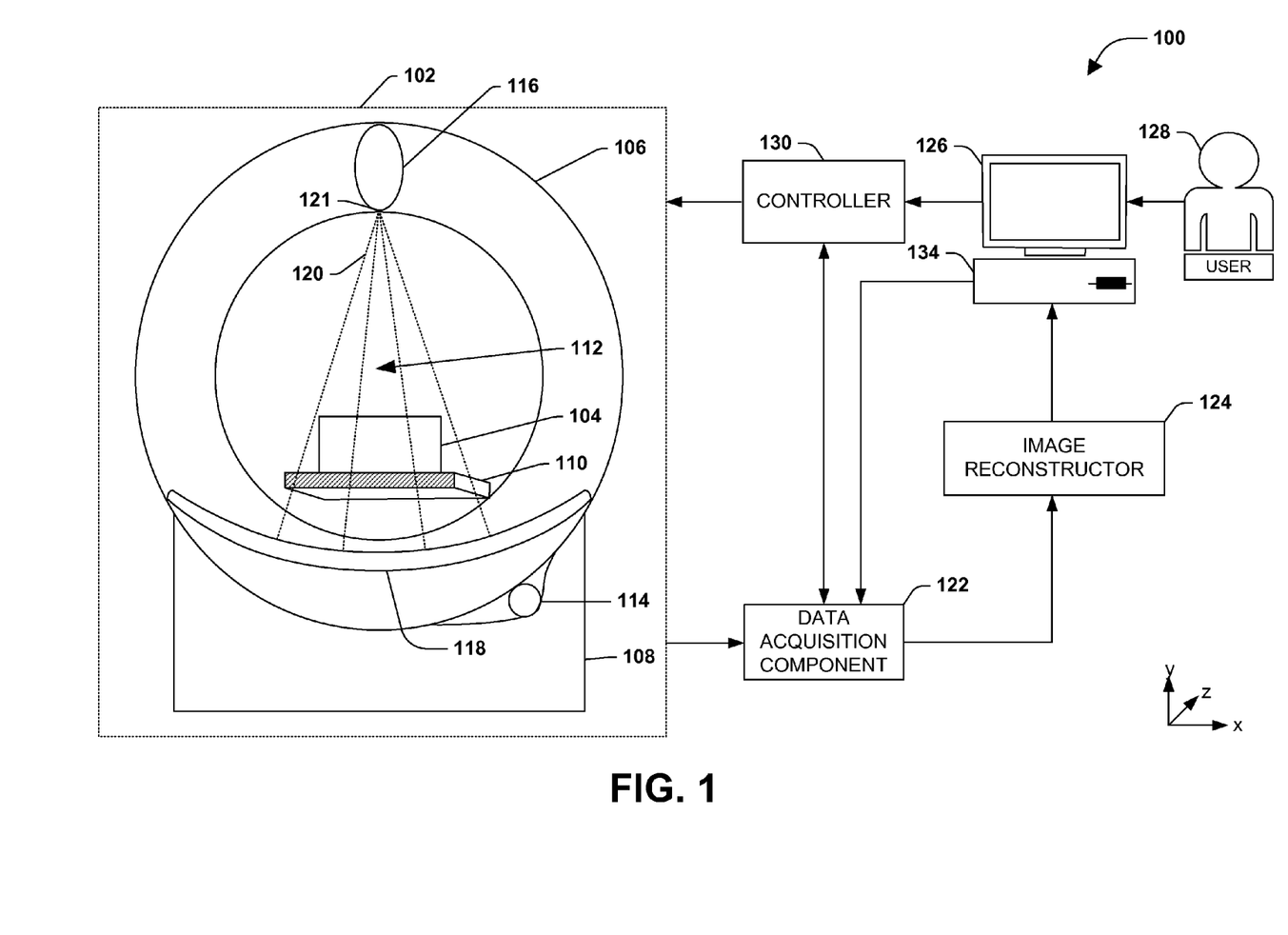
FIG. 1 is a schematic block diagram illustrating an example radiation system.

Aspects of the present application address the above matters, and others. According to one aspect, a data acquisition component is provided for an imaging system. The data acquisition component comprises a ramp generator configured to generate a ramp signal having a substantially parabolic voltage curve that comprises two substantially mirroring portions. The data acquisition component of the system also comprises a comparator configured to compare a first substantially mirroring portion of the ramp signal with a signal indicative of photons that are detected by a detector array 118 during an examination of an object. A second substantially mirroring portion provides a temporal delay such that circuitry of the ramp generator can settle.

According to another aspect, a method is provided. The method comprises generating a ramp signal that has a parabolic voltage curve comprising two substantially mirroring portions, where a first substantially mirroring portion allows a ramp generator to settle. Additionally, the method comprising comparing a second substantially mirroring portion of the ramp signal to a signal indicative of photons that are detected by a detector array during an examination of an object.

According to yet another aspect, a method for calibrating a ramp signal generator is provided. The method comprises receiving a ramp signal that has a parabolic voltage curve. The method also comprises identifying at least four points that intersect the parabolic voltage curve to determine a slope of the parabolic voltage curve. At least a first and a second point are indicative of a voltage associated with a substantially same number of photons. Further, the voltage is not a voltage that is generated when an associated radiation source is not activated, and the voltage is also not a voltage that can be generated when an air scan is performed.

According to another aspect, a computer readable medium is provided that comprises computer executable instructions that when executed via a processor on a computer perform a calibration method. The method comprises receiving a ramp signal having a parabolic voltage curve. The method also comprises identifying at least four points that intersect the parabolic voltage curve to determine a slope of the parabolic voltage curve. At least a first and second point are indicative of a voltage associated with a substantially same number of photons. The voltage is not a voltage that is generated when an associated radiation source is not activated and the voltage is not a voltage that is generated when an air scan is performed.

FIGURES

The application is illustrated by way of example and not limitation in the figures of the accompanying drawings, in which like references indicate similar elements and in which.

DESCRIPTION

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

FIG. 1 is an illustration of an example environment 100 in which data that is generated from components comprised within a rotating gantry 106 of a radiography scanner (e.g., a CT scanner) may be acquired so that one or more images of an object 104 under examination may be produced and displayed on a monitor 126, for example, such as for viewing by a human user 128. Such a scanner may be used to identify a tumor in a human patient at a medical center or in an animal at a veterinary clinic, and/or to identify objects of interest (e.g., potential threat objects, banned objects) associated with (e.g., comprising, comprised within, etc.) an object 104 (e.g., luggage) under examination at a security checkpoint, for example. In another embodiment, no image is generated, but the density and/or atomic characteristics of the object 104 can be identified and compared with a list of densities and/or atomic characteristics associated with predetermined items (e.g., banned items) to determine if the object 104 potentially comprises one or more of the predetermined items. It will be appreciated that while a CT scanning system is described herein, the instant application is not intended to be so limited. That is, to the extent possible, the instant application, including the scope of the claimed subject matter, is intended to be applicable to other systems as well. For example, the claimed subject matter is intended to be applicable to other radiographic systems, such as mammography systems, line scanners, etc., as well as photography systems, particle detection systems, and/or other imaging systems where discrete events are measured. It will also be appreciated that the example environment 100 merely illustrates an example schematic and is not intended to be interpreted as necessarily specifying the orientation of the components described herein. For example, a data acquisition component 122 as illustrated in FIG. 1, may be part of a rotating gantry 106 portion of the scanner.

In the example environment 100, the scanner comprises an object scanning apparatus 102 configured to examine one or more objects 104 (e.g., a series of suitcases at an airport, a human patient, etc.). The object scanning apparatus 102 can comprise a rotating gantry 106 and a stationary gantry 108. During an examination of the object(s) 104, the object(s) 104 can be placed on a support article 110, such as a bed or conveyor belt, that is selectively positioned in an examination region 112 (e.g., a hollow bore in the rotating gantry portion 106), and the rotating gantry 106 can be rotated about the object(s) 104 by a rotator 114 (e.g., motor, drive shaft, chain, etc.).

The rotating gantry 106 may surround a portion of the examination region 112 and comprises a radiation source 116 (e.g., an ionizing x-ray source) and a detector array 118 that is mounted on a substantially diametrically opposite side of the rotating gantry 106 relative to the radiation source 116 (e.g., where a focal spot 121 of the radiation source 116 would generally serve as a center of the detector array 118 should the detector array completely encircle the radiation source 116).

During an examination of the object(s) 104, the radiation source 116 emits radiation 120 towards the object(s) 104 under examination while the rotating gantry 106 (including the radiation source 116 and detector array 118) rotates about the object(s) 104. Generally, in a CT scanner, the radiation 120 is emitted substantially continuously during the examination. However, in some CT scanners and/or in other radiography scanners (e.g., pulsed radiography scanners), the radiation 120 may be emitted intermittently during the rotation.

As the radiation 120 traverses the object(s) 104, the radiation 120 may be attenuated differently by different aspects of the object(s) 104. Because different aspects attenuate different percentages of the radiation 120, an image may be reconstructed based upon the attenuation, or rather the variations in the number of photons that are detected by the detector array 118. For example, more dense aspects of the object(s) 104, such as a bone or metal plate, may attenuate more of the radiation 120 (e.g., causing fewer photons to strike the detector array 118) than less dense aspects, such as skin or clothing.

In some embodiments, while the object(s) 104 is being scanned, or examined, the object(s) 104 may be translated along an axis traveling in the z-dimension (if, as illustrated, the rotating gantry 106 is configured to rotate in an x, y plane). In this way, an object that has a z-dimension greater than the z-dimension of the radiation traversing the object may be scanned more quickly (relative to a step-and-shoot scanning approach). It will be appreciated that if the object(s) 104 is being translated (e.g., in the z direction) during a scan while the rotating gantry 106 is rotating (e.g., in the x, y plane), the scan may be referred to as a helical or spiral scan.

The detector array, which may be a direct conversion detector array (e.g., a detector array comprised of amorphous selenium photoconductors) and/or an indirect conversion detector array (e.g., a detector array comprised of a scintillator and a photodiode), is configured to convert the radiation photons into electrical charge that may be detected by one or more pixels, or elements, of the detector array 118 that are in close spatial proximity to the location where the radiation impinged. Respective pixels generate an analog signal (e.g., in a linear format) indicative of the electrical charge detected, which is fed to a data acquisition component 122. Because the electrical charge detected by the one or more pixels is directly related to the number of photons (e.g., an electrical charge of about 1200 electrons may be equivalent to one photon), the output is indicative of the attenuation of the radiation 120 as it traversed the object(s) 104. It will be appreciated that, in one embodiment, when a pixel is not detecting electrical charge, the pixel can emit an analog, baseline signal that indicates that the pixel has detected little to no electrical charge.

It will be understood to those skilled in the art that in some embodiments, an analog to digital (A/D) signal converter (not shown, but generally operably coupled with or comprised within the detector array 118 and/or the data acquisition component 122) may be configured to receive the analog signals and convert the signals into digital signals, as will be discussed in further detail below. The data comprised in the digital signals may be formatted in any one or more of a number of different formats, such as a 16-bit floating-point format, a quasi-logarithmic format, and/or a non-linear digital format, etc. Data comprised in the digital signals is commonly referred to in the art as projection space data because, like the analog signals, the digital signals are in projection space, and may represent an indication of how many photons are detected by a pixel.

In the example environment 100, signal data from the data acquisition component 122 is transmitted to an image reconstructor 124 configured to receive the projection space data, for example. The image reconstructor 124 is configured to reconstruct one or more images of the object 104 under examination using analytic, iterative, or other image reconstruction techniques known to those skilled in the art (e.g., 2D filtered back projection, tomosynthesis reconstruction, etc.). In this way, the data is converted from projection space to image space, a domain that may be more understandable by a user 128 viewing the image(s), for example.

The example environment 100 also includes a terminal 134 (e.g., a computer) configured to receive the image(s), which can be displayed on the monitor 126 to a user 128 (e.g., security personnel, medical personnel, etc.). In this way, a user 128 can inspect the image(s) to identify areas of interest within the object(s) 104. The terminal 134 can also be configured to receive user input which can direct the object scanning apparatus 102 how to operate (e.g., a speed to rotate, a speed of a conveyor belt, etc.) and/or can direct the monitor 126 to display an image of the object(s) 104 from a particular angle, for example.

In the example environment 100, a controller 130 is operably coupled to the terminal 134. In one example, the controller 130 is configured to receive user input from the terminal 134 and generate instructions for the object scanning apparatus 102 indicative of operations to be performed. For example, the user 128 may want to rescan the object(s) 104, and the controller 130 may issue an instruction instructing the support article 110 to reverse direction (e.g., bringing the object(s) 104 back into an examination region 112 of the object scanning apparatus 102).

Figure 2:
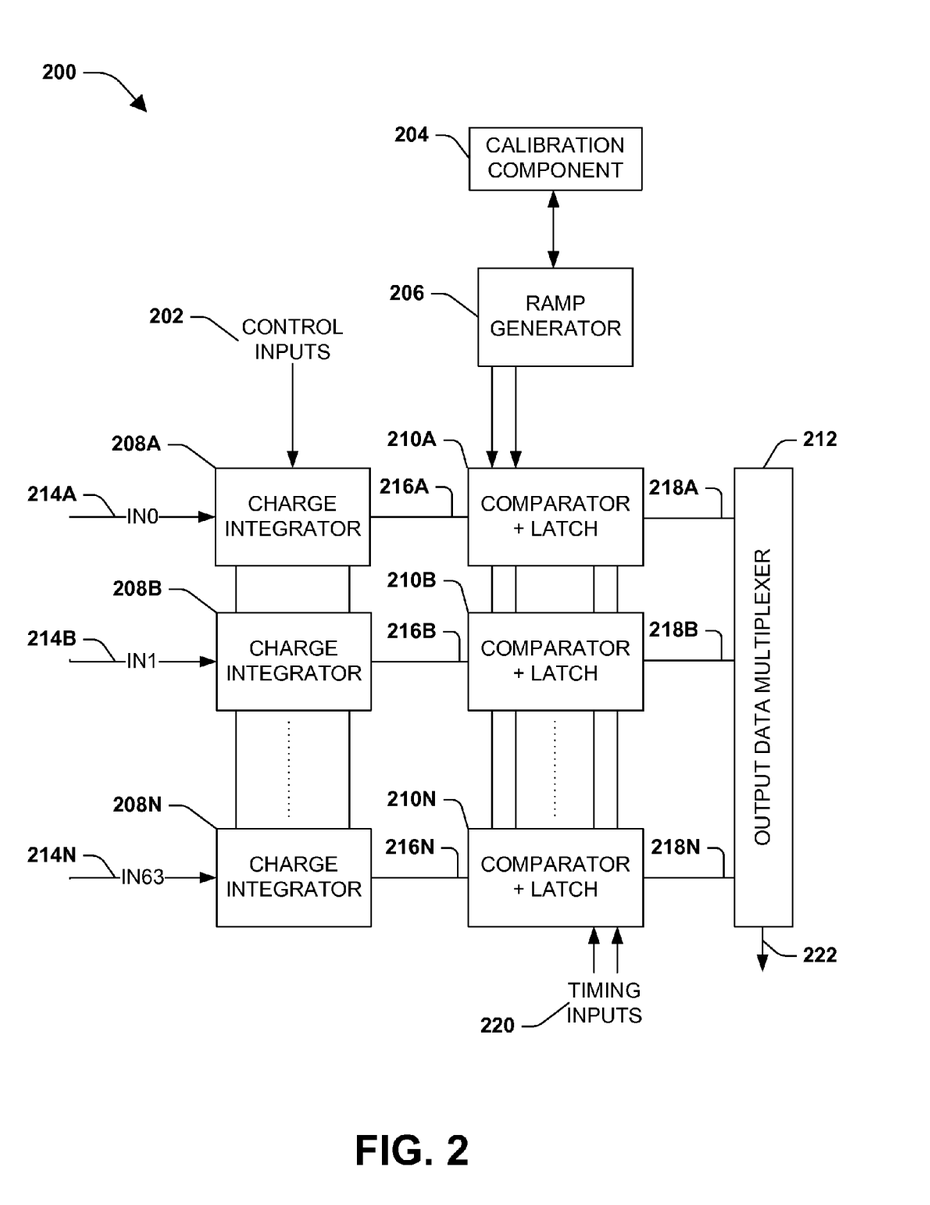
FIG. 2 is a component diagram illustrating one or more portions of an example data acquisition component.

FIG. 2 is a component diagram illustrating one or more portions of an example data acquisition component 200 (e.g., 122 of FIG. 1). The example data acquisition component 200 can comprise a charge integrator 208A, 208B, 208N (e.g., controlled by control inputs 202) that respectively convert an electrical current 214A, 214B, 214N indicative of a number of photons detected by a pixel, or proportional to a photon density measured by a pixel per unit time, into a voltage signal 216A, 216B, 216N indicative of a number of photons detected.

As an example, with reference to FIGS. 1 and 2, an object 104 can be scanned by the scanning apparatus 102, and the detector array 118 can detect radiation photons that impinge pixels (e.g., elements) of the array 118. In this example, the respective pixels detect electrical charge generated by the impinging radiation and output a current signal proportional to the detected electrical photon density per unit time. In this way, the current signals that are output by respective pixels are indicative of an amount of radiation that reached the detector array 118 at the respective pixels within a unit time.

Further, in this example, the output (e.g., the current signals) of the respective pixels can be received as one or more inputs for the data acquisition component 122 (e.g., 200 of FIG. 2). In one embodiment, the data acquisition component 200 can comprise a plurality of channels for receiving input signals (e.g., 214A, 214B, 214N) from the detector array 118. For example, a single data acquisition component chip may comprise 64 channels for receiving 64 input signals (e.g., illustrated in FIG. 2 as inputs IN0-IN63, 214A-214N), where respective channels receive an input from a corresponding pixel of the detector array 118. It will be appreciated that the data acquisition component 200 may be comprised of a plurality of data acquisition chips, such that the total number of channels is equal to the total number of pixels from the chips combined (e.g., which may be 10,000 or more), for example.

The example data acquisition component 200 also comprises a ramp generator 206 that generates a ramp signal to which one or more input signals may be compared, where the ramp signal has a substantially parabolic voltage curve. It will be appreciated that terms such as "parabolic" and/or "parabola", as well as like terms and variations thereof, are used herein in a broad sense to mean a symmetrical curve having two substantially mirroring portions. That is, a parabolic curve is intended to comprise a curve having a downward sloping portion that substantially mirrors an upward sloping portion. Moreover, the point where the downward and upward sloping portions of the curve meet may at times be referred to as the "apex" of the parabola. Accordingly, the instant disclosure and claimed subject matter is not intended to be limited to "U" shaped parabolas, such as those illustrated in FIGS. 3, 4 and/or 7, for example, but is instead intended to cover other types of symmetrical curves as well. As will be appreciated, utilizing such a ramp signal, in addition to allowing information to be ascertained about one or more input signals which are compared to the ramp signal, allows the ramp generator 206 to settle, among other things.

Figure 3:
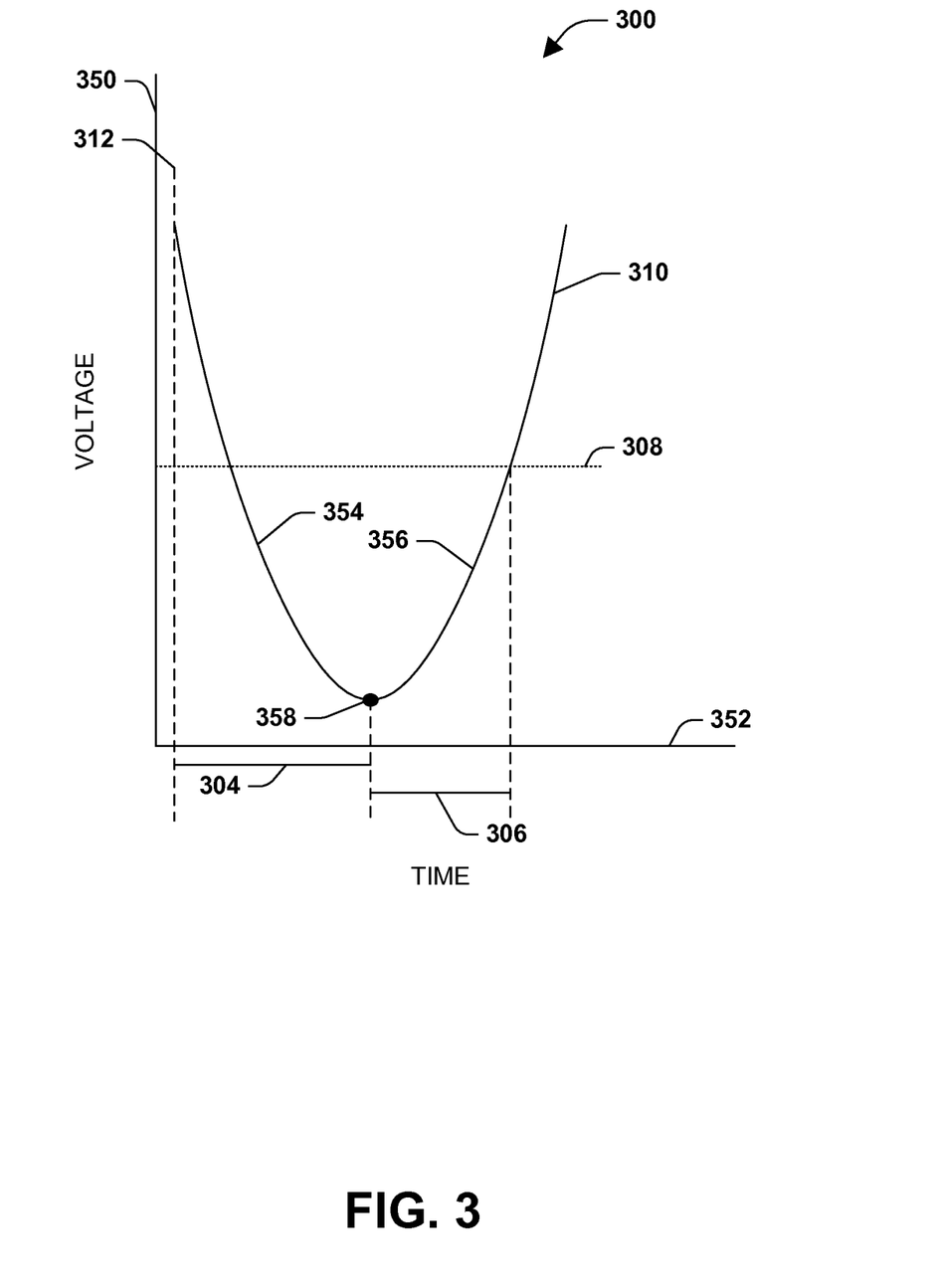
FIG. 3 is a graphical representation of an example ramp signal having a substantially parabolic curve.
Figure 4:
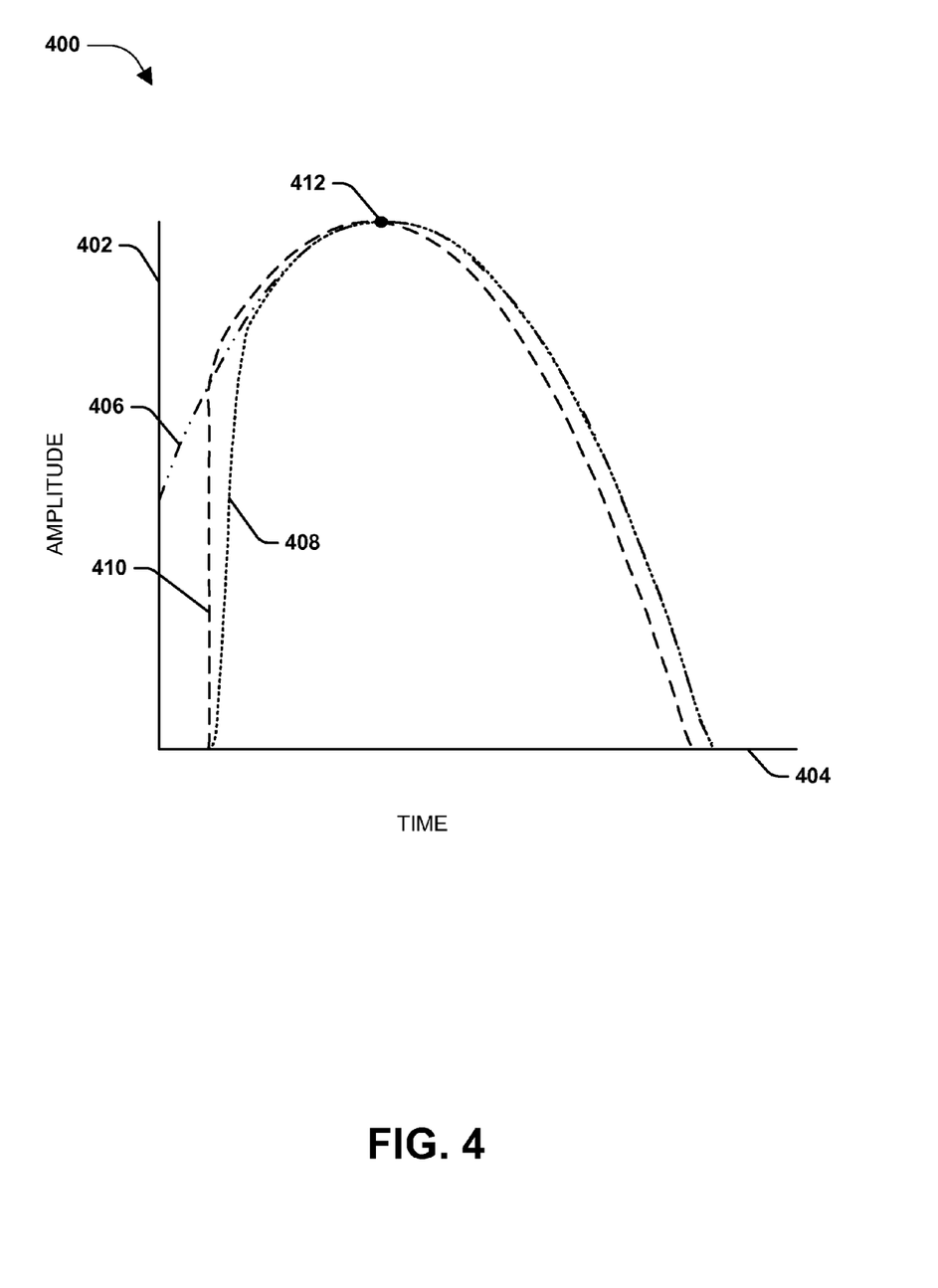
FIG. 4 is an illustration of example ramp signals, at least some of which may be output by a ramp generator.

FIG. 3 is a graphical representation 300 of an example ramp signal having a substantially parabolic curve (e.g., as output from ramp generator 206 of FIG. 2). In this example 300, a 'Y' axis 350 comprises a voltage for the ramp signal, and an 'X' axis 352 comprises a time for the ramp signal. Further, as described above, the substantially parabolic voltage curve of the ramp signal comprises two substantially mirroring portions 354 and 356. The mirroring portions 354 and 356 are two halves of the parabolic curve divided at the apex 358. It will be appreciated that the orientation of the parabola may differ from the orientation of the example ramp signal 310. That is, the slope and/or direction of the slope may differ from that illustrated. For example, the ramp signal 310 may begin with a downward sloping curve (e.g., as illustrated in FIG. 3) or an upward sloping curve (e.g., as illustrated in FIG. 4). Nevertheless, as just mentioned, a parabola as used herein is intended to comprise a symmetric curve.

It will be appreciated that a parabolic ramp signal provides numerous benefits over other linear and/or non-linear ramp signals that are used to digitize signals yielded from detected radiation. For example, a parabolic ramp signal allows data to be quantized in fewer bits relative to other types of ramp signals, and since a ramp signal is used to measure the time until a comparator (e.g., 210A, 210B, 210N in FIG. 2) triggers, fewers bits means that a time resolution of a digital-analog converter portion of the data acquisition component (e.g., 200 in FIG. 2) can be decreased, or the sample speed can be increased. Additionally, by reducing the time resolution, a clock interpolator (e.g., outputting timing inputs 220 in FIG. 2) could be eliminated in favor of a more stable crystal clock signal, for example. Reducing the number of bits also reduces power consumption because there are fewer time steps (e.g., there are fewer flips at a latch of an associated comparator (e.g., 210A, 210B, 210N) at respective channels). Thus, by using a parabolic ramp signal and reducing the number of bits, the power consumption of a data acquisition chip of a data acquisition component (e.g. 200 in FIG. 2) can be reduced, the sample speed can be increased, and/or the complexity of the conversion can be reduced. Moreover, it will be appreciated to those skilled in the art that by reducing the number of bits, the amount of data that is transmitted between the data acquisition component and other components of a radiography examination apparatus is reduced (e.g., and less data compression may be required), for example.

There are different techniques for generating a ramp signal having a substantially parabolic curve. A first example technique implemented with regard to a ramp generator utilizes two integrators (e.g., one or more of which may be comprised within the ramp generator), where a first integrator produces a linear ramp signal from a constant voltage reference input to the ramp generator; and a second integrator integrates the ramp signal to produce the parabolic curve. A second example technique that can be implemented with regard to the ramp generator uses a digital to analog converter (e.g., that may be comprised within the ramp generator) to produce the parabolic curve. It may be appreciated that filtering may be implemented with one or more of the techniques to reduce noise, for example.

FIG. 4 is a graphical illustration 400 of an example where a ramp signal 408 is produced that substantially corresponds to a best fit parabolic curve 406 (e.g., an ideally shaped curve). More specifically, FIG. 4 illustrates three curves, a first curve is a best fit parabolic curve 406 (e.g., a theoretical curve that the ramp generator is attempting to form), an initial ramp signal 410 (e.g., a curve that is formed before filtering has been applied to the ramp signal), and a filtered ramp signal 408 (e.g., a signal that is formed after the initial ramp signal 410 is filtered) that is output from the ramp generator. It will be appreciated that while the curves in FIG. 4 may be inverted relative to the curves in FIGS. 3 and 7, for example, such curves may be compared to one another merely by inverting one or more of the curves again. In the illustrated example, the graph comprises a "Y" axis illustrating amplitude 402, such as in volts, and an "X" axis illustrating time 404, such as in seconds or milliseconds. As illustrated, a digital to analog converter, for example, yields an initial ramp signal 410 that has a shape that is similar to the best fit parabolic curve 406 (e.g., the desired output ramp signal), but does not substantially align with the best fit parabolic curve 406. The initial ramp signal 410 is then, for example, passed through one or more filters (e.g., a low-pass filter, etc.) to yield a filtered ramp signal 408 that substantially aligns with the best fit parabolic curve 406. It should be noted that, as illustrated, the filtered ramp signal 408 does not initially align with the best fit parabolic curve 406 because the ramp generator (e.g., 206 in FIG. 2) is settling. However, as will be discussed below, this portion of the parabolic curve is used to settle the ramp generator and will be not be used to determine a digital value for an unknown voltage signal (e.g., because the filtered ramp signal 408 is not substantially ideal while the ramp generator is settling).

Returning to FIG. 2, the example data acquisition component 200 comprises a comparator 210A, 210B, 210N, which compares a first substantially mirroring portion of the ramp signal (e.g., 310 of FIG. 3) with a voltage signal indicative of photons that are detected by a detector array of the radiography system during an examination of an object (e.g., 216A, 216B, 216N). Further, a second substantially mirroring portion of the ramp signal, which is not used for comparing against the signal indicative of detected photos, is used to, among other things, provide a temporal delay so that circuitry of at the ramp generator 206 can settle to, among other things, mitigate the effects of noise. That is, the second substantially mirroring portion of the signal, which may not align with a best fit parabolic curve (e.g., 406 in FIG. 4), is used to settle the ramp generator 206, for example, such that the portion of the parabolic ramp signal that is compared to the signal indicative of the number of photons detected (e.g., the first substantially mirroring portion) substantially aligns with the best fit parabola (e.g., in FIG. 4, the filtered voltage ramp signal 408 substantially aligns with the best first parabola after the apex 412 such that the signal indicative of the number of photons detected is compared to a substantially ideal ramp signal (e.g., to give a less noisy/more accurate indication of the number of photons actually detected)). It is to be appreciated that "first" and "second" as used herein to modify "substantially mirroring portions" are not intended to be limited to indicating parts used for comparison and settling, respectively. That is, a portion of a curve used for comparison is not always referred to as the first portion, and a portion of a curve used for setting is not always referred to as the second portion. For example, in one or more other embodiments, a part of a curve used for settling may be regarded as a first portion of the curve and a part of the curve used for comparison may be regarded as a second portion of the curve. Essentially, first and second are just used as modifiers to indicate different parts of a curve.

As illustrated in the example graphical representation 300 of a filtered ramp signal 310 of FIG. 3 (e.g., 408 in FIG. 4), the first substantially mirroring portion 356 of the ramp signal 310 (e.g., the portion after the apex 412 in FIG. 4) can be compared with a photon detection signal 308 (e.g., 214A, 214B, 214N/216A, 216B, 216N of FIG. 2 infra), which is indicative of a number of photons detected by a pixel of the detector array. In this embodiment, this portion 356 of the ramp signal 310 comprises a measurement period 306, during which a measurement of the photon detection signal 308 can be made. For example, the measurement period 306 can comprise a time period that begins at the apex 358 of the parabolic ramp signal 310, and ends when the ramp signal 310 and the photon detection signal 308 are equivalent (e.g., intersect). Nevertheless, the measurement period could also include some of portion 354 of the ramp signal 310, such as where the ramp generator settles more quickly, for example (e.g., filtered voltage ramp signal 408 substantially matches best fit curve 406 more quickly or before the apex 412 in FIG. 4).

Further, the second substantially mirroring portion 354 of the ramp signal 310 (e.g., the portion before the apex 412 in FIG. 4) can be used as a "settling" period 304 (e.g., temporal delay), which can comprise a period for circuitry to "settle," for example. Stated differently, while the ramp generator (e.g. 206 in FIG. 2) is settling, the ramp signal that is produced may not be ideal (e.g., because the ramp generator is charging). A non-ideal ramp is undesirable for measurement because it does not follow a predetermined path (e.g., a best fit parabolic curve (e.g., 406 in FIG. 4)), and therefore, if it is it used for measurement purposes, it may introduce inaccuracy into the resulting digital signal. Thus, the second substantially mirroring portion 354 is used merely to settle the ramp generator and is generally not used for measuring the photon detection signal 308. Moreover, it will be appreciated that having such a settling period allows for a lower bandwidth circuit to be used in the ramp generator because the ramp generator does not have to produce a parabolic voltage curve quickly upon being triggered 312 (e.g., by the terminal 134 in FIG. 1). That is, the ramp generator can more slowly gear up to producing a substantially ideal parabolic ramp signal because of the settling period 304. It will be appreciated that using a lower bandwidth circuit also generally reduces the amount of noise generated by the ramp signal, which is an added benefit of using the settling period 304 to settle the ramp generator.

Returning to FIG. 2, the ramp generator 206 can generate the ramp signal, such as illustrated as 310 in FIG. 3, which comprises a parabolic voltage ramp signal (e.g., 310 in FIG. 3). In one embodiment, the ramp signal (e.g., 310 in FIG. 3) generated by the ramp generator 206 is utilized by the respective comparators 210A-210N, such that a substantially same ramp signal may be utilized by a plurality of comparators substantially concurrently, for example.

Returning to FIG. 3, the voltage level 350 is measured over time 352, and during a settling period 304, the parabolic voltage curve of the ramp signal 310 comprises a downward slope 354, where, as mentioned above, this may allow the ramp generator circuits to "settle" to reach correct values. That is, the ramp signal can be started "prematurely" so that by a time of comparison (e.g., measurement period 306) at least some inaccuracy associated with the ramp generator has been reduced. In this embodiment, the measurement period 306 begins at the apex 358 and continues at least until the ramp signal 310 and photon measurement voltage signal 308 are equivalent (e.g., intersect).

Returning to FIG. 2, a latch (e.g., associated with the comparator 210) can be used to generate data that indicates a time when an output of the comparator changes. For example, with reference to FIG. 3, when the ramp signal 310 meets the input signal 308 (e.g., both signals have equivalent voltage 350) the latch can be activated, at which point the comparator output is changed. To further illustrate, in this example, while the latch is not activated the comparator output (e.g., 218A, 218B, 218N) may comprise a zero value (e.g., as a binary form); and when the latch is activated, the comparator output may comprise a (binary) one, therefore comprising a change in state/value.

When the comparator output changes, in one embodiment, a time value 352 can be determined; this time value can comprise a digital representation of the input signal 216 to the comparator 210. For example, a photon received by an pixel on the detector array (e.g., 118 of FIG. 1) may represent a particular voltage (e.g., one photon equals 5 µV), for example. In this example, a time value can be measured from the time of the apex 358 of the parabolic voltage ramp signal 310 until the time the two signals are equivalent (or substantially equal due circuit delays, etc.).

In one embodiment, the time value (e.g., time for the measurement period 306) can be combined with a time interpolator (e.g., time between timing pulses) for timing input pulses 220 of FIG. 2 generated by a timing component (not shown). For example, the timing component may emit timing pulses to the comparator and latch component 210 at known intervals (e.g., 1.25 nanoseconds), and the number of pulses comprised in the measurement period 306 (e.g., rounded up or down to a whole number) can represent the time value for the input signal 216 to the comparator 210. In this way, in this example, the voltage signal input representing the number of photons detected (e.g., 216) can be converted to a digital representation (e.g., 218), indicated by a whole number representing a number of pulses during the measurement period 306.

In the embodiments described above, the downward slope of the parabolic voltage curve (e.g., 354) generated by the ramp generator is utilized as the "settling" period, and the upward slope (e.g., 356) is utilized for the measurement period. In another embodiment, the parabolic voltage curve (e.g., 310) may comprise an initial upward slope extending to the apex, and a secondary downward slope extending from the apex (e.g., an upside down version of the example 300). In this embodiment, the comparator may compare the downward sloping portion of the ramp signal with the signal indicative of the photons detected, and the upward sloping portion may provide the settling period (temporal delay).

It will be appreciated that the ramp generator (e.g., which may be a circuit) may not produce an exact replica of a predetermined ramp (e.g., a best fit parabolic curve 406 in FIG. 4) due to manufacturing, hardware and/or other variations, etc. (e.g., the parabolic voltage curve may be off by +/−100 mV from expectations/specifications). Therefore, a specific nature of the parabolic voltage curve generated by a particular ramp generator at a particular time (e.g., filtered ramp signal 408 of FIG. 4) can be identified at some desired calibration interval (e.g., for respective scans) in order to provide a correction (calibration) to an output of a comparator (e.g., 218 output by 210 of FIG. 2). In one embodiment, a mathematical derivation of the output signal can be used to correct (calibrate) in accordance with the calibration determination.

Accordingly, in the example data acquisition component 200 of FIG. 2, a calibration component 204 is included and is configured to determine a slope of the parabolic voltage ramp signal (e.g., 310 of FIG. 3, 408 of FIG. 4). In one embodiment, the calibration component 204 determines the slope of the parabolic voltage curve by identifying four points on the parabolic voltage curve. In this embodiment, at least two of the points on the curve intersect the curve at different points and represent a substantially same, generally unknown, voltage (e.g., 308 in FIG. 3); therefore, these points also represent a substantially same number of detected photons (but where the actual number of detected photons may be unknown). Because these two points generally represent the same voltage or number of detected photons, they are at times referenced as a single point (and thus calibration may be regarded as being performed with three (instead of four) points). Further, in this embodiment, the voltage represented by these two points is not a (e.g., minimum) voltage generated when an associated radiation source is not activated (e.g., no radiation is emitted from a radiation source); and the voltage represented by these two points is not a (e.g., maximum) voltage that is generated when an air scan (e.g., scanning the scan area 112 of FIG. 1 without an object 104 present) is performed.

In one embodiment, another relevant point on the curve can be an "offset" point which can be determined by generating a voltage signal from the scanning device (e.g., 102 of FIG. 1) without emitting radiation (e.g., the source is deactivated). In this embodiment, the voltage signal generated is generally indicative of zero or a substantially minimum number of detected photons, as little to no radiation is emitted during the scan. Therefore, for example, the voltage signal merely comprises electronic offsets, providing an offset measurement to a signal from a scan using radiation. In this example, the offset measurement can represent a minimum voltage generated by a scan.

In one embodiment, another relevant point on the curve can be a "gain" point which can be determined by generating a voltage signal from the scanning device, while emitting a substantially maximum amount of scanning radiation, without an object in the scanning area of the scanner (e.g., an "air scan"). In this embodiment, the voltage signal generated is generally indicative of a substantially maximum number of detected photons, as little to none of the radiation is attenuated in the scanning area, for example. Therefore, the voltage signal provides a gain measurement for the parabola, for example, representing a substantially maximum voltage that can be generated by a scan.

Having identified the gain and offset points of the parabolic voltage curve, the calibration component 204 can identify the third point by finding the aforementioned at least two points on the curve that intersect the curve at different points, representing the substantially same voltage, thereby representing the substantially same number of detected photons. For example, a voltage signal can be introduced to the comparator (e.g., between the gain and offset voltage levels), and time measurements can be taken (e.g., using the timing inputs 220 and latch) to identify the time of the first intersection of the known signal with the parabolic curve, and the time of the second intersection of the known signal with the parabolic curve. It will be appreciated that by identifying these two times, a third point (e.g., corresponding to third and fourth points) on the parabolic voltage curve can be identified, for example, thereby allowing the ramp signal to be calibrated (e.g., the actual ramp signal generated by the particular hardware, etc. comprising the ramp generator (e.g., 206 of FIG. 2) can be determined). It will be appreciated that because these two points are at the same voltage level, the apex of the parabola can also be identified as being somewhere on a line (e.g., extending in the y direction in FIG. 3) midway between the third and fourth points.

Stated differently, in order to determine the slope of a unique second order function, such as a parabola, at least three points are generally needed/determined. While two points can be determined based upon the gain (e.g., a measurement taken during an air scan while radiation is emitted at full power) and an offset (e.g., a measurement taken while substantially no radiation is emitted), it is generally difficult to expose the data acquisition component to a specified level of radiation photons in between the gain and the offset because the radiation source is generally not linear (e.g., the radiation source cannot precisely emit a specified number of radiation photons). Thus, in one embodiment (e.g., by taking advantage of the non-monotonic nature of the parabola), measurements of a first source on both sides of the parabola may be taken. It will be appreciated that the midpoint of these two measurements may be used to determine the time of the parabola inflection (e.g., the apex) regardless of the actual level measured (so long as the same level is measured for both sides of the parabola).

It will be appreciated that where a four point calibration technique is used as described herein, the ramp signal may settle before the apex (e.g., rather than at the apex), such that the ramp signal is substantially settled at both points where the unknown voltage signal and the ramp signal intersect. It will also be appreciated that while the calibration component 204 is said to use four points to determine the slope of the parabolic voltage curve, as discussed above the slope of the parabolic voltage curve can be said to be determined by identifying three points of the curve as at least two points of the curve may be consolidated since they represent a same voltage (e.g., if a precise voltage can be generated by the x-ray source and/or can be applied to the detector array). However, generally, in practice, such a precise voltage cannot be generated so the calibration generally uses four points, at least two of which represent a substantially same voltage. It will also be appreciated that "substantially" is at times used herein at least because quantum mechanics may come into play when detecting or otherwise dealing with photons, and thus the exact or actual number of photons may be difficult if not impossible to determine, such that detection of a number of photons within a tolerance or standard deviation is standard practice.

It will be appreciated that such a calibration procedure is further discussed below with respect to FIGS. 6 and 7.

Returning to FIG. 2, an output data multiplexer 212 may be used to receive the digital outputs 218A, 218B, 218N of the comparators 210A, 210B, 210N, for example, and generate an appropriate output 222 for an associated image reconstruction component (e.g., 124 of FIG. 1), which may be sent to an image reconstructor (e.g., 124 in FIG. 1), for example.

Figure 5:
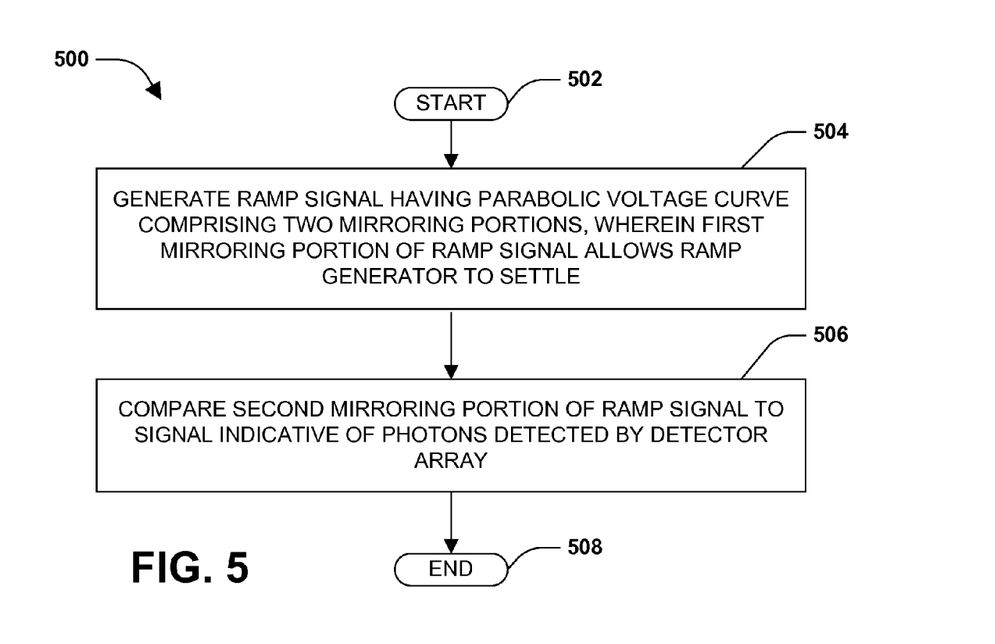
FIG. 5 is a flow diagram of an example method for using a parabolic voltage curve as a ramp signal.

FIG. 5 is a flow diagram illustrating an example method 500 for using a parabolic voltage curve as a ramp signal, where both (mirroring) halves of the curve are utilized. The example method 500 begins at 502 and involves generating a ramp signal that has a parabolic voltage curve comprising two substantially mirroring portions, where a first mirroring portion of the ramp signal allows a ramp generator to settle, at 504. When a parabola is divided in half along an axis from the parabola's apex, the two halves are mirror images of each other. For example, a downward sloping portion of the parabola (e.g., from a start point to an apex) can be a mirror image of an upward portion of the parabola (e.g., from the apex to an end point).

In one embodiment, the settling period may comprise a propagation delay, which may be a period during which both an input voltage (e.g., input to charge and/or a signal for the circuit) and an output voltage for the circuit becomes stable and valid. In this way, for example, ramp inaccuracy can be mitigated by allowing for the ramp generator to properly "settle," prior to beginning an input comparison. In one embodiment, the first portion of the ramp signal (e.g., comprising the settling period) provides the ramp generator time for their respective signals to reach a desired voltage level accuracy threshold (e.g., 90% of specification).

In one embodiment, the first substantially mirroring portion of the ramp signal can comprise the downward slope portion of the parabolic voltage curve, for example, where the settling period begins at a start point on the curve and ends at an apex of the curve. In another embodiment, the parabolic voltage curve may be inverted, for example, where the first substantially mirrored portion comprises an upward slope, having an apex at a top of the curve. In this embodiment, the upward portion can comprise the "settling" period for the ramp generator.

At 506 of the example method 500, a second substantially mirroring portion of the ramp signal is compared to a signal that represents a number of photons detected by a detector array of an imaging system during an examination of an object. In one embodiment, the signal that represents the number of photons detected by the detector array comprises the second input signal to the comparator, where the first input signal is the ramp signal. In this embodiment, the second input signal represents a number of photons, where a greater number of photons provides a higher voltage signal.

In this embodiment, for example, the ramp signal can be used to help determine the voltage level of the second input signal. Because the ramp signal is known (e.g., as generated by the ramp generator), the voltage of the ramp signal at a point in time is also known. In one embodiment, the ramp generator can be triggered to generate the ramp signal, and the settling period can occur between the triggering and a generation of an apex of the ramp signal. In this embodiment, a measurement period can then begin at the apex of the ramp signal, and continue until the ramp signal and the second input signal are equivalent (e.g., may not be exactly the same but within some desired threshold of equivalence due to potential error, delay, etc. inherent in circuitry).

In one embodiment, the second substantially mirroring portion of the ramp signal can comprise the upward sloping portion of the parabolic voltage curve, for example, where the measurement period begins at the apex point on the curve and ends at some point of the curve where the two input signals are (substantially) equivalent. In another embodiment, the parabolic voltage curve may be inverted, for example, where the second substantially mirrored portion comprises a downward slope, having an apex at a top of the curve. In this embodiment, the downward portion can comprise the "measurement" period for the ramp generator and/or comparator.

In one embodiment, a digital time signal can be "latched" when the comparison performed by the comparator causes a change in an output from the comparison. For example, the comparator can utilize a binary output whereby the output comprises either a zero or one. In this example, the comparator output may start at zero when the two input signals are initiated and received by the comparator, and change to one when the two input signals are substantially equivalent. In this embodiment, when the comparator output changes from zero to one, for example, the digital time signal can be latched, thereby marking a time when the two input signals (e.g., ramp voltage signal and photon level voltage signal) are substantially equivalent.

In one embodiment, a number of photons detected, such as by a detector array of the radiography scanner, can be determined based on the latched digital time signal. That is, for example, the measurement period can be determined by counting a number of timer pulses (e.g., from a digital timing component) between the apex of the parabolic voltage ramp signal (e.g., ramp signal as the first input to the comparator) and the time of the latching (e.g., when the photon detection voltage signal, as the second input to the comparator, is equivalent to the first input).

Having compared the second mirroring portion of the ramp signal to the photon indication signal, the example method 500 ends at 508.

Figure 6:
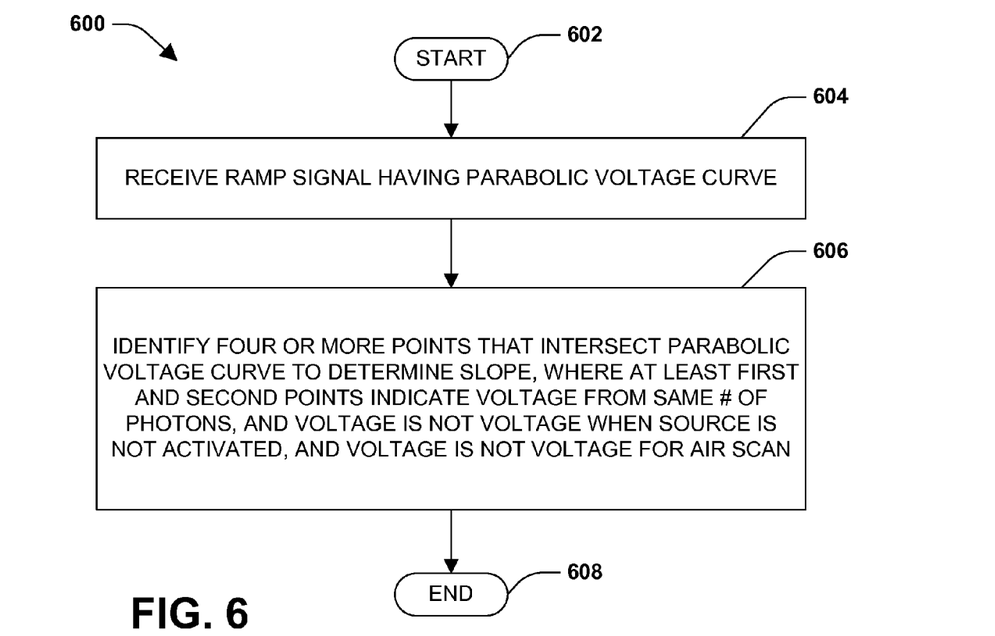
FIG. 6 is a flow diagram of an example method for calibrating a non-linear, single slope converter.

FIG. 6 is a flow diagram of an example method 600 for calibrating a ramp signal generator. The example method 600 begins at 602 and involves receiving a ramp signal having a parabolic voltage curve, at 604. As an illustrative example, FIG. 7 is an example graphical representation 700 of a parabolic ramp voltage signal 720. In this example 700, a "Y" axis represents a number of photons 716, such as generated from a detection array in a radiography scanning device, where the number of photons is represented by a voltage proportional to the number detected, for example. Further, a "X" axis represents time 714 during which the parabolic ramp signal is generated.

Figure 7:
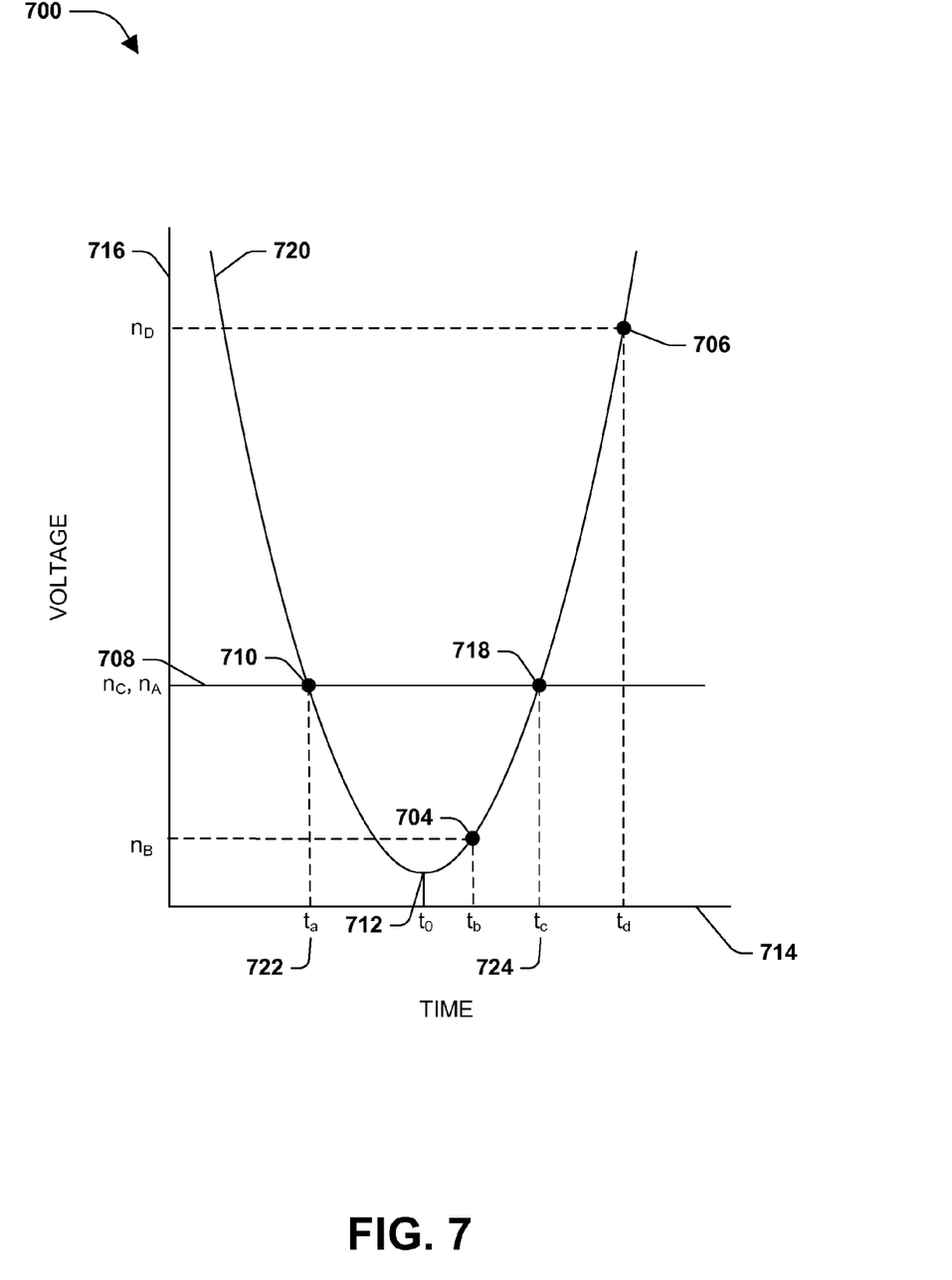
FIG. 7 is a graphical representation of an example parabolic ramp voltage signal.

Returning to FIG. 6, at 606 in the example method 600, at least four points are identified that intersect the parabolic voltage curve (e.g., 720 of FIG. 7). The four points are identified to determine a slope for the parabolic voltage curve, for example, thereby identifying a particular function and shape of the parabola. In this example, at least a first and a second point are representative of a voltage associated with a substantially same number of detected photons, and thus at times may be referred to as a single point (e.g., if a sufficiently precise voltage can be generated by the x-ray source and/or can be applied to the detector array). Further, the voltage indicated for the first and second points is not a (e.g., minimum) voltage that can be generated when an associated radiation source is not activated (e.g., little to no radiation is emitted) during a scan; and the voltage indicated is also not a (e.g., maximum) voltage that can be generated when an air scan is performed.

Turning to FIG. 7, as an illustrative example, a signal 708 indicative of a first voltage can be input to a comparator while the ramp signal 720 is being input to the comparator. For example, to input such a signal, a scan can be performed using a phantom (e.g., an object of known characteristics) that allows a predetermined amount of photons (within reasonable tolerances) to pass through the phantom and impinge the detector array. In this way, a first, constant voltage may be produced. When the signal 708 intersects with the ramp signal 720 (e.g., the two signals are substantially equivalent), a time at the first point of intersection 710 can indicate a first time measurement $t_a$ 722. Further, when the signal 708 intersects with the ramp signal 720 at a second time, a time at the second point of intersection 718 can indicate a second time measurement $t_c$ 724. It will be appreciated that the apex 712 of the parabola is located at a time substantially half-way between $t_a$ 722 and $t_c$ 724.

In one embodiment, a third point on the parabola may be indicative of a substantially maximum voltage signal, such as generated when an air scan is performed; and a fourth point may be indicative of a substantially minimum voltage, such as generated when little to no radiation is emitted from a radiation source during a scan. In FIG. 7, a gain measurement 706 for the parabola can be determined by running the scanner at substantially maximum radiation, while no object is present in the scanning area. In this way, for example, little to none of the radiation is attenuated by an object, so a substantially maximum amount is detected by the detection array. Therefore, in this example, the voltage signal 706 produced by such an air scan indicates a substantially maximum voltage signal point on the parabolic curve 720.

Additionally, an offset measurement 704 for the parabola can be determined by running the scanner with little to no radiation (e.g., source deactivated), while no object is present in the scanning area. In this way, for example, little to no radiation is detected by the detection array. Therefore, in this example, the voltage signal produced by such a scan indicates merely electronic offset associated with the electronics, and a substantially minimum offset measurement 704 on the parabolic curve 720 can be identified. In this embodiment, having determined at least four points, the "actual" parabolic curve generated by the ramp generator can be identified (e.g., the function and/or slope for the curve). In this way, for example, the "actual" parabolic curve can be used to calibrate any results returned by the comparator. That is, the parabolic curve identified by the at least four points is a characteristic curve of the circuitry used to generate the curve, and since this same circuitry will be used when an object is scanned, the results from a scan can be adjusted accordingly.

Stated differently, the relationship between the number of photons detected (N) and a time output of the analog-digital converter (e.g., 218A, 218B, 218N in FIG. 2) can be written as:

$$N = C_1(t-t_0)^2 - N_0.$$

Where $C_1$ is a constant, $t_0$ is a time when the parabola reaches the apex, and $N_0$ is the number of photons measured at the apex. As illustrated in FIG. 7, $t_0$ can be solved because $n_a$ is equal to $n_c$. Thus:

$$t_0 = \frac{t_A + t_C}{2}.$$

During an offset measurement, $n_B$ substantially no photons are being detected so $n_B$ can be set equal to zero. Thus, $N_0$ can be written as:

$$N_0 = C_1(t_0 - t_0)^2.$$

During a gain measurement, a full scale number of photons (F.S.), $n_d$ (e.g., a maximum possible number of photons) are detected, and therefore:

$$F.S. + N_0 = C_1(t_D - t_0)^2.$$

Solving these two equations for the two unknowns, $N_0$ and $C_1$ can be solved as a function of F.S. Thus, $$N_0 = \frac{F.S.(t_B - t_0)^s}{(t_D - t_0)^2 - (t_B - t_0)^2},$$

and $$C_1 = \frac{F.S.}{(t_D - t_B)^3 - (t_B - t_3)^2}.$$

With all three variables (e.g., $C_1$, $N_0$, and $t_0$) known, the number of photons, N, can be solved as a ratio to F.S. given any time measurement, t. Thus, $$N = \frac{F.S.}{\left(t_D - \frac{t_{A+t_C}}{2}\right)^s - \left(t_B - \frac{t_{A+t_C}}{z}\right)^z}\left(t - \frac{t_A + t_C}{2}\right)^2 -$$

-continued $$\frac{F.S.\left(t_B - \frac{t_A + t_C}{z}\right)^z}{\left(t_D - \frac{t_{A+t_C}}{2}\right)^z - \left(t_B - \frac{t_{A+t_C}}{3}\right)^2}$$

Thus, the slope of a parabolic ramp signal can be identified based upon four measurements (or three measurements if a sufficiently precise voltage can be generated by the x-ray source and/or can be applied to the detector array). This characteristic curve of the ramp generator can then be used to make desired adjustments, such as to an output of a comparator (e.g., 218 output by 210 of FIG. 2) so that less skewed or noisy results may be provided (e.g., since the same ramp generator is used in practice).

Returning to FIG. 6, having identified at least four points for the parabolic curve, the example method 600 ends at 608.

Figure 8:
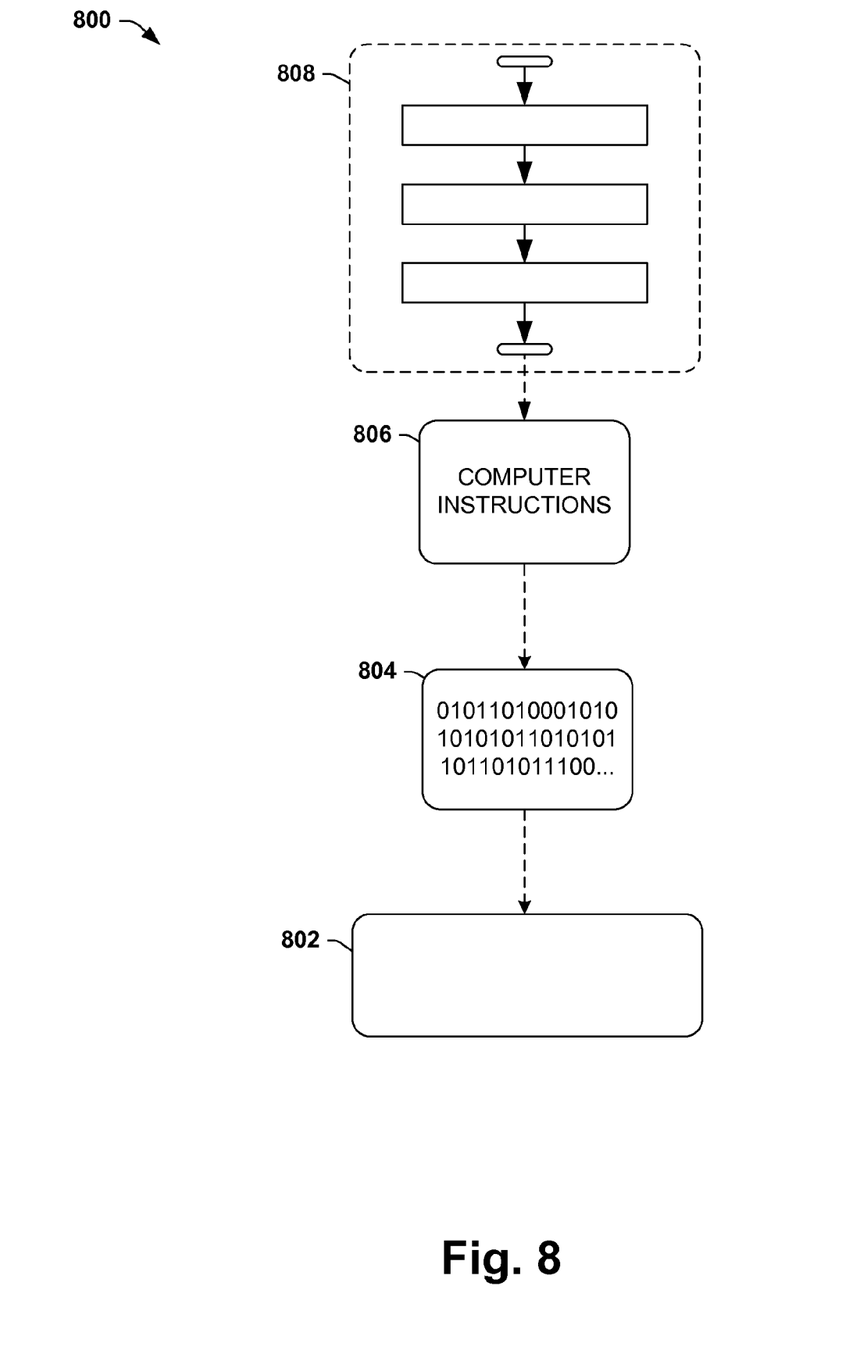
FIG. 8 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 8, wherein the implementation 800 comprises a computer-readable medium 802 (e.g., a flash drive, CD-R, DVD-R, or a platter of a hard disk drive), on which is encoded computer-readable data 804. This computer-readable data 804 in turn comprises a set of computer instructions 806 configured to operate according to one or more of the principles set forth herein. In one such embodiment 800, the processor-executable instructions 806 may be configured to perform a method 808, such as the example method 600 of FIG. 6, for example. In another such embodiment, the processor-executable instructions 806 may be configured to implement a system, such as at least some of the exemplary system 100 of FIG. 1, for example. Many such computer-readable media may be devised by those of ordinary skill in the art that are configured to operate in accordance with one or more of the techniques presented herein.

It will be appreciated to those skilled in the arts that there are numerous benefits to one or more of the systems and/or techniques described herein. For example, the use of both sides of a parabolic-shaped ramp signal allows the ramp generator to settle before a measurement is made. In this way, a substantially perfect/ideal parabolic curve can be compared to the unknown voltage signals generated by respective pixels of the detector array. Moreover, the use of a settling period allows for the implementation of lower bandwidth circuits (e.g., because the ideal parabolic curve does not have to be created as quickly) than those traditionally used for non-linear ramp generators. Further, a calibration technique for determining the actual shape of the parabola can be used that takes advantage of both sides of the parabolic-shaped ramp signal.

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A data acquisition component for an imaging system, comprising:
   a ramp generator configured to generate a ramp signal having a substantially parabolic voltage curve that comprises two substantially mirroring portions; and
   a comparator configured to compare a first substantially mirroring portion of the ramp signal with a signal indicative of photons that are detected by a detector array during an examination of an object, wherein a second substantially mirroring portion provides a temporal delay such that circuitry of the ramp generator can settle.

2. The data acquisition component of claim 1, comprising a charge integrator configured to convert an electrical current indicative of photons that are detected by the detector array into a voltage signal indicative of photons that are detected by the detector array, wherein the comparator is configured to compare the voltage signal with the first substantially mirroring portion of the ramp signal.

3. The data acquisition component of claim 1, comprising a latch configured to generate data indicative of a time when an output of the comparator changes.

4. The data acquisition component of claim 1, comprising a calibration component configured to determine a slope of the parabolic voltage curve.

5. The data acquisition component of claim 4, wherein the calibration component is configured to determine the slope of the parabolic voltage curve based upon four points that intersect the parabolic voltage curve, wherein at least two of the points are indicative of a voltage associated with a substantially same number of photons, wherein the voltage is not a dark scan voltage that is generated when an associated radiation source is not activated, and wherein the voltage is not an air scan voltage that is generated when an air scan is performed.

6. The data acquisition component of claim 1, wherein the first substantially mirroring portion of the ramp signal comprises an upward-sloping portion of the ramp signal and the second substantially mirroring portion of the ramp signal comprises a downward-sloping portion of the ramp signal.

7. The data acquisition component of claim 1, wherein the first substantially mirroring portion of the ramp signal comprises a downward-sloping portion of the ramp signal and the second substantially mirroring portion of the ramp signal comprises an upward-sloping portion of the ramp signal.

8. The data acquisition component of claim 1, wherein the data acquisition component is part of a radiation system comprising an ionizing radiation source.

9. A method, comprising:
   generating a ramp signal having a parabolic voltage curve comprising two substantially mirroring portions, where a first substantially mirroring portion allows a ramp generator to settle; and
   comparing a second substantially mirroring portion of the ramp signal to a signal indicative of photons that are detected by a detector array during an examination of an object.

10. The method of claim 9, wherein the detector array is part of a radiation system.

11. The method of claim 9, wherein the first substantially mirroring portion of the ramp signal comprises a downward-sloping portion of the ramp signal and the second substantially mirroring portion of the ramp signal comprises an upward-sloping portion of the ramp signal.

12. The method of claim 9, wherein the first substantially mirroring portion of the ramp signal comprises an upward-sloping portion of the ramp signal and the second substantially mirroring portion of the ramp signal comprises a downward-sloping portion of the ramp signal.

13. The method of claim 9, comprising latching a digital time signal when the comparison causes a change in an output derived from the comparison.

14. The method of claim 13, comprising determining a number of photons detected based on the latched digital time signal.

15. The method of claim 9, comprising determining a slope of the parabolic voltage curve, the determination comprising identifying at least four points that intersect the parabolic voltage curve, wherein at least two of the points are indicative of a voltage associated with a substantially same number of photons, wherein the voltage is not a dark scan voltage that is generated when an associated radiation source is not activated, and wherein the voltage is not an air scan voltage that is generated when an air scan is performed.

16. The method of claim 9, wherein the first substantially mirroring portion of the ramp signal provides a period of time for a ramp generator signal to reach a desired voltage level accuracy threshold.

17. The method of claim 9, comprising triggering a ramp generator to generate the ramp signal, wherein a settling period elapses between the triggering and a generation of an apex of the ramp signal, wherein a measurement period begins at least at the apex.

18. The method of claim 17, wherein the measurement period begins during the first substantially mirroring portion of the ramp signal at a time when the ramp generator has substantially settled.

19. A method for calibrating a ramp signal generator, comprising:
   receiving a ramp signal having a parabolic voltage curve; and
   identifying at least four points that intersect the parabolic voltage curve to determine a slope of the parabolic voltage curve, wherein at least a first and a second point are indicative of a voltage associated with a substantially same number of photons, wherein the voltage is not a dark scan voltage that is generated when an associated radiation source is not activated, and wherein the voltage is not an air scan voltage that is generated when an air scan is performed, at least some of the method implemented at least in part via a processing unit.

20. The method of claim 19, comprising:

identifying a characteristic of the ramp signal generator based upon the identified at least four points; and making an adjustment to a signal based upon the identified characteristic.

21. The method of claim 19, wherein a third point is indicative of a maximum voltage that is generated when the air scan is performed and a fourth point is indicative of a minimum voltage that is generated when no radiation is emitted from the associated radiation source.

22. A non-transitory computer readable medium comprising computer executable instructions that when executed via a processing unit perform a calibration method comprising:

receiving a ramp signal having a parabolic voltage curve; and identifying at least four points that intersect the parabolic voltage curve to determine a slope of the parabolic voltage curve, wherein at least a first and a second point are indicative of a voltage associated with a substantially same number of photons, wherein the voltage is not a dark scan voltage that is generated when an associated radiation source is not activated, and wherein the voltage is not an air scan voltage that is generated when an air scan is performed.

* * * * *